(12) United States Patent
Moon

(10) Patent No.: US 8,389,030 B2
(45) Date of Patent: Mar. 5, 2013

(54) NEMATICIDES FROM JUGLANDACEAE AND METHODS OF USE THEREOF

(75) Inventor: Darin J. Moon, Burley, ID (US)

(73) Assignee: Redox Chemicals, Inc., Burley, ID (US)

( * ) Notice: Subject to any disclaimer, the term of this patent is extended or adjusted under 35 U.S.C. 154(b) by 0 days.

(21) Appl. No.: 13/027,985

(22) Filed: Feb. 15, 2011

(65) Prior Publication Data

US 2011/0165278 A1    Jul. 7, 2011

Related U.S. Application Data

(62) Division of application No. 11/792,029, filed as application No. PCT/US2005/043484 on Nov. 30, 2005, now Pat. No. 7,927,635.

(60) Provisional application No. 60/632,082, filed on Nov. 30, 2004.

(51) Int. Cl.
| | |
|---|---|
| A01N 65/00 | (2009.01) |
| A61K 36/20 | (2006.01) |
| A61K 36/40 | (2006.01) |
| A61K 36/44 | (2006.01) |
| A61K 36/49 | (2006.01) |
| A61K 36/52 | (2006.01) |
| A61K 36/63 | (2006.01) |
| A61K 36/76 | (2006.01) |

(52) U.S. Cl. ...................................... 424/771
(58) Field of Classification Search .............. 424/771
See application file for complete search history.

(56) References Cited

U.S. PATENT DOCUMENTS

| | | | | |
|---|---|---|---|---|
| 5,250,500 | A * | 10/1993 | Jones et al. .................... | 504/165 |
| 6,164,244 | A * | 12/2000 | Cutler et al. ................... | 119/215 |
| 6,284,948 | B1 | 9/2001 | Jessen et al. | |
| 6,296,838 | B1 * | 10/2001 | Bindra et al. ................... | 424/61 |
| 6,565,867 | B1 * | 5/2003 | O'Leary ....................... | 424/405 |
| 6,749,848 | B2 | 6/2004 | Chen | |
| 2002/0132021 | A1 | 9/2002 | Raskin et al. | |
| 2004/0185123 | A1 | 9/2004 | Mazzio et al. | |
| 2007/0264369 | A1 | 11/2007 | Moon | |

FOREIGN PATENT DOCUMENTS

WO    WO 2006/060582    6/2006

OTHER PUBLICATIONS

Mahajan et al. Nematol. Medit (1992), 20: 217-219.*
Kempster, doctoral dissertation, University of Adelaide, 2000.*
All Allergy (Zing Solutions, 1998): http://www.allallergy.net/fapaidfind.cfm?cdeoc=1613.*
Cline and Neely (Phytopathology 74:185-188; 1984).*
Swiecki et al. (American Journal of Botany vol. 69, No. 1 (Jan. 1982), pp. 141-149).*
Sholberg and Gaunce (Crop Protection, vol. 15, Issue 8, Dec. 1996, pp. 681-686 ).*
Klocke (Allelochemicals: Role in Agriculture and Forestry, Chapter 36, pp. 396-415, ACS Symposium Series, vol. 330, Publication Date (Print): Jan. 8, 1987).*
Bhargava et al. (Journal of Pharmaceutical Sciences vol. 57, Issue 10, pp. 1728-1732, Oct. 1968).*
Cypser et al., "Multiple stressors in Caenorhabditis elegans induce stress hormesis and extended longevity," 2002, J. of Gerontol A. Biol. Sci. Med Sci., 57(3), pp. P109-B114. Abstract.
Duke, Stephen O.; "Natural pesticides from plants"; *Advances in New Crops*; 1990; appl. 511-517; Timber Press, Portland, Oregon.
Ercisli et al., "The allelopathic effects of juglone and walnut leaf extracts on yield, growth, chemicals and PNE compositions of strawberry cv. Fern," 2005, Plant Soil Environments, 51(6): 283-287.
Fraser et al., "Primary Screening of Copper Compounds for Herbicidal, Nematocidal, Fungicidal and Bactericidal Activity," A Sep. 16, 1974, Incra Rep. pp. 43; Report No. Incra Project No. 211.
Heisey et al, "Antifeedant Effects fop land extracts on Colorado Potato Beetle," 2001, Journal of the Pennsylvania Academy of Science, 74(2-3); pp. 52-56, (Abstract Only).
International Search Report Dated May 16, 2006, issued in related International Patent Application No. PCT/US2005/043784, filed Nov. 30, 2005.
Isman, Murray B., et al.; "Tropical Timber Species as Sources of Botanical Insecticides"; *Phytochemicals for Pest Control*; 1997; pp. 27-37; American Chemical Society; Washington, D.C.
Kaku, Allison M.; "The Effect of Walnut Extract on Root Lesion Nematodes"; California State Science Fair Project Summary; 2002.
Krajci, W.M. and D.L. Lynch; "The inhibition of various microorganisms by crude walnut hull extracts and juglone"; *Microbios Letters*; 1977; pp. 175-181; vol. 4.
Pattigan, Dustin J.; "Alternatives to Methyl Bromide"; California State Science Fair Project Summary; 2003.
Pinkerton et al., "Effects of Biologically Derived Products on Mobility and Reproduction of the Root Lesion Nematode, Pratylenchus Penetrans, on Strawberry," 2007, Nematroopica, 36(2), pp. 176-190.
Shrestha, "Potential of a Black Walnut(Juglans Nigra) Extract Product (NatureCur®) as a Pre and Post-Emergence Bioherbicide," 2009, Journal of Sustainable Agriculture, 33(8), pp. 810-822.
Wuyts, Nathalie, et al.; "Effects of plant secondary metabolites on plant parasitic nematodes"; Symposium Poster Session; 2002; http://www.ifns.org/cd2002/VISKAS/243.pdf.
Daglish, C., "The Isolation and Identification of a Hydrojuglone Glycoside Occurring in the Walnut," 1950, Biochem J, vol. 47(4), pp. 452-457.
Cline, S., and Neely, D., "Relationship Between Juvenile-Leaf Resistance to Anthracnose and the Presence of Juglone and Hydrojuglone Glucoside in Black Walnut," 1984, Phytopathology, vol. 74(2), pp. 185-188.

*Primary Examiner* — David J Blanchard
*Assistant Examiner* — Devang Thakor
(74) *Attorney, Agent, or Firm* — Kilpatrick Townsend & Stockton LLP

(57) ABSTRACT

The invention provides compositions and methods for inhibiting nematode damage to plants. The compositions comprise acid extracts or alcohol extracts from juglone-producing members of the Juglandaceae. The methods comprise applying the compositions of the invention to soil contacting roots of nematode-susceptible plants.

22 Claims, 2 Drawing Sheets

US 8,389,030 B2

NEMATICIDES FROM JUGLANDACEAE AND METHODS OF USE THEREOF

CROSS-REFERENCES TO RELATED APPLICATIONS

This application is a divisional application of U.S. application Ser. No. 11/792,029, filed Jul. 18, 2007, now U.S. Pat. No. 7,927,635, which is a national stage entry of PCT/US05/43484, filed Nov. 30, 2005, which claims priority to U.S. Provisional Application No. 60/632,082, filed Nov. 30, 2004, the contents of which are hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Nematodes (sometimes known as "roundworms") are the most common multi-cellular animals on earth. There are thousands of species. While most species are not harmful to plants, unfortunately, some are plant parasites. Some, such as pin nematodes (*Paratylenchus*) and stubby-root nematodes (*Trichodorus* and *Paratrichodorus*), live outside the plant (that is, they are ectoparasites) pierce root cells with a body part known as the stylet and suck out the content of root cells. Others, such as root-lesion nematodes (*Pratylenchus*) enter the plant root and move through it, weakening the root system. Root-knot nematodes (*Meloidogyne*) enter the roots as juveniles and release chemicals which cause the formation of visible galls or "root knots".

As a group, nematodes cause millions of dollars of damage to turf grasses, corn and other vegetable crops, cotton plants, and fruit trees. Methods of control include rotating crops and application of chemicals. Biological means such as nematophagous fungi (see, e.g., U.S. Pat. No. 6,749,848) have been tried, as have methods such as introducing nucleotide sequences that confer resistance (see, e.g., U.S. Pat. No. 6,284,948). Chemicals such as organophosphates have been the major commercially used technique for controlling nematodes. Unfortunately, they are toxic to wildlife, and their use is being restricted or terminated due to environmental concerns. Nemacur®, the only nematicide approved in various states for use on plants after they have been planted ("post plant"), is highly toxic to fish and wildlife. By agreement with the U.S. Environmental Protection Agency, the manufacturer will not be able to sell it after May 2007.

According to Duke, S. O. "Natural pesticides from plants", pp. 511-517, in J. Janick and J. E. Simon (eds.), ADVANCES IN NEW CROPS, (Timber Press, Portland, Oreg., 1990), many plant species, such as marigolds, chrysanthemums, castor bean, margosa, and some members of the family Asteraceae are resistant to nematodes. The reference indicates that the active principle for the nematicidal activity has not been discovered in all of these examples and that no plant-derived products were being sold commercially for control of nematodes.

Juglone is a naphtaquinone produced by members of the Juglandaceae, and particularly plants of the genus *Juglans*. It is exuded particularly by the black walnut; juglone is toxic to a number of commercially valuable plant types, which therefore cannot be grown in proximity to walnut trees. Juglone is only slightly soluble in water and does not travel very far through the soil. Its toxicity to other plants occurs when the roots of the juglone-producing tree come in close proximity to the roots of a susceptible plant.

In 2001, Wuyts et al. presented a poster stating that juglone had some toxicity to the endoparasitic nematode *Pratylenchus penetrans*. Unfortunately, the inability of juglone to travel far through the soil and its toxicity to many commercially valuable plants makes its use as a nematicide in the field problematic. In 2002, a California state science fair project summary reported that a walnut extract made from steeping cut up branches of walnut in water had some toxicity to root lesion nematodes placed in the extract. In 2003, however, a further California state science fair project summary reported on tests of the ability of methyl bromide, methyl iodide, walnut "tea" extract, and commercial compost to disinfest plant roots of root-knot nematodes. This project summary reported that the walnut tea extract failed to disinfest the soil of the nematodes.

It would be desirable to have alternative means to inhibit nematode infestations of plants.

BRIEF SUMMARY OF THE INVENTION

The present invention provides compositions that inhibit nematode growth and methods for doing so. In a first group of embodiments, the invention provides composition comprising an acid extract or an alcohol extract of material from a first juglone-producing plant of the family Juglandaceae. In some embodiments, the first juglone-producing plant is a member of a genus selected from the group consisting of *Carya, Engelhardtia, Juglans, Platycarya* and *Pterocarya*. In some embodiments, the plant is a member of the genus *Juglans*. In some embodiments, the plant is of a species selected from the group consisting of *J. nigra, J. cinerea*, and *J. regia*. In some embodiments, the plant is *J. nigra*. In some embodiments, the material from which the extract is made is selected from the group consisting of nut hull, leaf, nut shell, root, bark, and wood.

In some embodiments, the extract is made from nut hull. In some embodiments, the extract is an acid extract. In some embodiments, the acid extract is an extract made using an organic acid. In some embodiments, the acid is selected from acetic acid and citric acid. In some embodiments, the extract is an alcohol extract, and the composition further comprises an organic acid or acid anhydride. In some embodiments, the alcohol used for the alcohol extraction is ethanol. In some embodiments, the organic acid is a carboxylic acid. In some embodiments, the acid is selected from the group consisting of acetic acid and citric acid. In some embodiments, the composition further comprises a surfactant. In some embodiments, the composition further comprises an emulsifier. In some embodiments, the emulsifier is a potassium phosphate. In some embodiments, the potassium phosphate is tetrapotassium pyrophosphate.

In some embodiments, the composition further comprises a plant systemic inducer. In some embodiments, the plant systemic inducer is selected from the group consisting of salicylic acid, jasmonic acid, isonicotinic acid, dichloroisonicotinic acid, phosphorous acid, cinnamic acid, chitosan, humic acid, and a beta-1,3 glucan. In some embodiments, the plant systemic inducer is salicylic acid. In some embodiments, the composition comprises both an acid extract and an alcohol extract of the first juglone-producing plant. In some embodiments, the composition further comprises an acid extract or alcohol extract of a second juglone-producing plant of the family Juglandaceae. In some embodiments, the first and said second juglone-producing plants are of the genus *Juglans*. In some embodiments, the first and second juglone-producing plants are selected from the group consisting of *J. nigra*, *J. cinerea*, and *J. regia*, provided that said first and said second juglone-producing plants are not of the same species. In some embodiments, the material from which the extract from said second juglone-producing plant is made is selected from the group consisting of nut hull, leaf, nut shell, root, bark, and wood. In some embodiments, the extract of the second juglone-producing plant is an alcohol extract and the alcohol is ethanol. In some embodiments, the extract of said second juglone-producing plant is an alcohol extract and the composition further comprises an organic acid or acid anhydride. In some embodiments, the composition comprises an acid extract of said first juglone-producing plant and an alcohol extract of said second juglone producing plant.

In a further group of embodiments, the invention provides methods of inhibiting nematode damage to a first plant. The methods comprise applying to soil contacting the roots of the plant an extract of material from a juglone-producing plant of the family Juglandaceae, said extract selected from the group consisting of an acid extract and an alcohol extract of said material, wherein contacting said soil with said extract kills nematodes in said soil, thereby inhibiting nematode damage to said first plant. In some embodiments, the juglone-producing plant is a member of a genus selected from the group consisting of *Carya*, *Engelhardtia*, *Juglans*, *Platycarya* and *Pterocarya*. In some embodiments, the juglone-producing plant is a member of the genus *Juglans*. In some embodiments, the juglone-producing plant is of a species selected from the group consisting of *J. nigra*, *J. cinerea*, and *J. regia*. In some embodiments, the juglone-producing plant is *J. nigra*. In some embodiments, the material from which the extract is made is selected from the group consisting of nut hull, leaf, nut shell, root, bark, and wood. In some embodiments, the extract is an alcohol extract and the alcohol is ethanol. In some embodiments, the extract is an alcohol extract and the composition further comprises an organic acid or acid anhydride. In some embodiments, the organic acid is a carboxylic acid. In some embodiments, the carboxylic acid is selected from the group consisting of acetic acid and citric acid. In some embodiments, the extract is an acid extract. In some embodiments, the acid extract is made with a carboxylic acid. In some embodiments, the carboxylic acid is selected from the group consisting of acetic acid, peracetic acid, and citric acid. In some embodiments, the extract further comprises a surfactant. In some embodiments, the extract further comprises an emulsifier. In some embodiments, the emulsifier is a potassium phosphate. In some embodiments, the extract comprises both an acid extract of said material and an alcohol extract of said material. In some embodiments, the method comprises contacting the soil with an alcohol extract of a first juglone-producing plant and an acid extract of a second juglone-producing plant. In some embodiments, the extract is of at least two juglone-producing plants of the family Juglandaceae. In some embodiments, the plant as to which nematode damage is to be inhibited and the juglone-producing plant used to produce the extract are of the same species.

DETAILED DESCRIPTION OF THE INVENTION

Introduction

Figure 1:
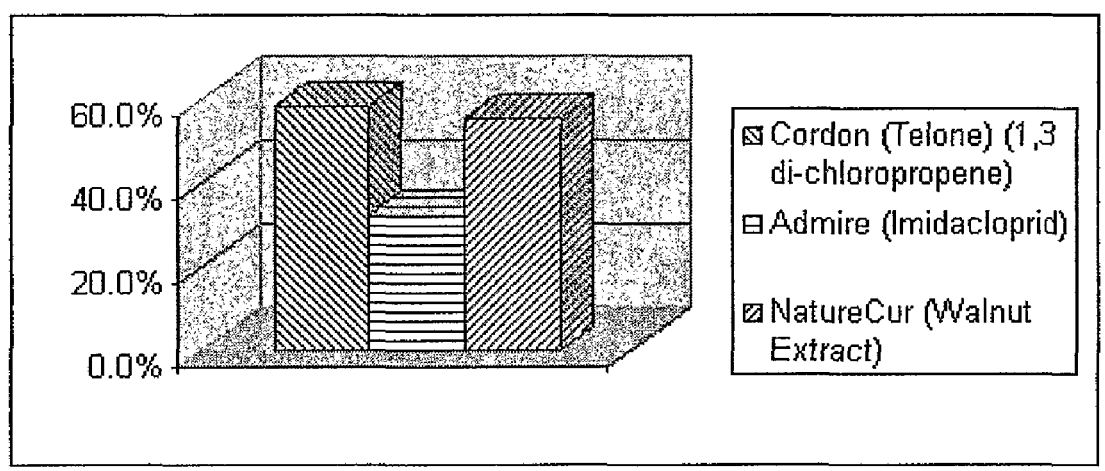
FIG. 1 is a graph of the percent reduction in nematode infestation of soil after the soil was treated with the agent indicated, compared to untreated soil. Vertical axis: percent reduction of nematodes. Legend: bar with lines sloping downward from left to right: 1,3 dichloropropene; bar with horizontal lines, imidacloprid; bar with lines sloping upward from left to right, an alcohol extract of the invention.

Surprisingly, it has now been discovered that extracts prepared by steeping materials from juglone-producing member of the family Juglandaceae, and particularly from trees of the genus *Juglans* in an acid solution, or, even more preferably, an alcohol solution, results in compositions with dramatic anti-nematode activity. The compositions are effective in reducing nematode numbers on plants in the field and their high activity permits sharply reducing the amount of the composition that needs to be applied in the field. Moreover, the high anti-nematode activity of the compositions means they can be applied as concentrations that do not inhibit the growth of juglone-sensitive plants. Thus, the invention provides a new method of protecting plants from nematode infestations by reducing nematode infestations prior to planting (pre-plant) and after the soil has been planted (post-plant).

Studies underlying the present invention indicate that the compositions of the invention are surprisingly more useful as a field agent against nematodes than is pure juglone, which is apparently the only component of walnut extracts previously identified as having anti-nematode activity. The poster by Wuyts et al. noted in the Background section reported that, under in vitro conditions, juglone was lethal to half a population of the nematode *P. penetrans* at concentrations of 90 parts per million ("ppm") (the dose of an agent required to kill 50% of a population is known as its "$LD_{50}$"; thus, juglone had an $LD_{50}$ of 90 ppm on *P. penetrans*) after exposure for 72 hours.

It is known, however, that it is fairly easy to kill nematodes while they are bathed in water under in vitro conditions. Under such conditions, the nematodes are in constant contact with whatever agent is in the water, and there are no interactions that might ordinarily occur between the agent and the multitude of organic and inorganic compounds present in normal soils. In field use, however, it is impracticable to flood a field with a solution of juglone for a period of days to keep nematodes in contact with the juglone. Moreover, juglone is not very soluble in water and does not move far in soil, while for effective control of nematodes it is generally desirable to kill the nematodes in the top 12 inches of soil. Thus, a solution of juglone and water may be suitable for use as a nematicide in hydroponic applications, but is generally not suitable for use as a nematicide on plants growing in soil.

In contrast, the compositions and methods of the invention have been shown to be effective in the field, and can be used to penetrate the soil to protect the bulk of the root mass. Moreover, the compositions can be applied without the need to modify traditional farm watering and fertilizer application equipment. The compositions of the invention can be applied at rates which render them commercially viable compared to the chemically based nematicides that would otherwise be needed. Further, since the compositions of the invention are far less toxic to handle and apply than conventional pesticides, use of the compositions and methods of the invention reduces the exposure of farmers and agricultural workers to toxic chemicals they may be poorly trained or equipped to use. And, since the compositions are both relatively non-toxic to produce and much less environmentally damaging to use than conventional nematicides, the invention provides meaningful protection from nematodes at sharply cost to the environment. Finally, as noted above, the protection has been demonstrated with respect to a variety of plants. Thus, the compositions and methods of the invention provide an easy and cost effective substitute for toxic chemical nematicides.

The compositions of the invention are surprisingly more effective than are extracts of similar plant materials using water. Assigning a water extract of the plant materials a nematode-killing value of one for comparison purposes, the studies underlying the present invention found that acid-based extracts of the plant materials were approximately 50% more effective in killing nematodes. Two alcohols were used: glacial acetic acid and a 30% solution of citric acid in water. Each was used to extract material from plant material, and each gave an extract with nematode-killing activity about 50% higher than extracting the plant materials with water.

Surprisingly, extractions of similar plant material with alcohol resulted in extracts which were some 80% more effective in killing nematodes than a water-only extract from the same material. Using an extract made by steeping the plant material with an alcohol, and then adding an acid and surfactants to the extract, as discussed below, resulted in compositions with about 100% more activity than did a water-only extract of the same plant material. Thus, the invention provides new compositions that are surprisingly more effective at killing nematodes than water-based extracts.

Interestingly, juglone-producing plants are themselves subject to nematode attack. It is expected that the compositions and methods of the invention will be useful in inhibiting nematode attack on juglone-producing plants as well as on plants that do not produce juglone.

Definitions

"Juglone" is a compound known chemically as 5-hydroxy-1,4-naphthoquinone, or 1,5-dihydroxy-4-naphthalenyl-β-glucopyranoside. It is available commercially from, for example, the Calbiochem division of EMD Biosciences, Inc. (San Diego, Calif.).

The term "crop," as used herein usually refers to plants raised in fields in an agricultural setting, and includes, along with carrots, tomatoes, grapes, oranges, and other plants intended for human or animal consumption, plants intended for use as fibers, plants to be used as or processed into medicaments, plants grown for fragrance, flowers, herbs, and decorative, recreational, and ornamental plants. In this context, the term includes tree farms, such as those growing conifers to be used as Christmas trees, and grasses grown for use as turf. The term can also encompass plants grown hydroponically, or preferably, in soil, in greenhouses.

The terms "plant systemic inducer," "systemic inducer of resistance," and "systemic inducer" are used herein as synonyms and as used herein refer to chemical or biological agents that induce pathogen resistance after a plant is contacted with a plant systemic inducer. Examples of chemical plant systemic inducers include, inter alia, salicylic acid, jasmonic acid, isonicotinic acid, dichloroisonicotinic acid, phosphorous acid, and cinnamic acid, chitosan, humic acid, and beta-1,3 glucans and other mixed glucans.

One skilled in the art will recognize that biological plant systemic inducers include, inter alia, bacteria, viruses, fungi, and nematodes. Kelp, a form of seaweed, and some other seaweeds, are rich sources of beta glucans and can be used as systemic inducers in the compositions and methods of the invention. Unlike bacteria, viruses, and most other microbiological agents, kelp and other seaweeds are sold commercially as fertilizers and are available as liquid extracts or as dried powders. In this regard, they more resemble agricultural chemicals and for ease of discussion, will therefore be treated as chemical inducers herein unless otherwise indicated. Finally, humic acid, a component found in the humus portion of some soils, also acts as a systemic inducer. Thus, the term "systemic inducer" can, where appropriate, include reference to humic acid. In preferred embodiments, we have found good results by including humic acid along with other systemic inducers in the compositions and methods of the invention. Accordingly, the addition of humic acid to other systemic inducers will generally be specifically denoted herein.

Contacting "soil in contact with the roots of a plant" with a composition of the invention refers to soil in sufficiently close proximity to the roots of plants intended to be treated that the amount of the composition applied can be reasonably expected to reach the roots of the target plants. With respect to crops in a field or trees in a grove, for example, the phrase refers to soil surrounding the roots of the crops in that field or the trees in that grove.

As used herein, reference to an "acid extract" or to an "alcohol extract" of plant material refers to the liquid product resulting from steeping the plant material for a given period of time in an acid solution (to create an acid extract) or in an alcohol solution (to create an alcohol extract). For convenience of reference, use of the term "extract" herein refers to an acid extract or to an alcohol extract except where it is clear in context that the reference is to an extract made by steeping a plant material solely in water.

The phrase "reactive oxygen species" (abbreviated herein as "ROS") describes oxygenated compounds which serve as a source of oxygenated radicals. The term is considered to be synonymous with "activated oxygen species." These compounds include, inter alia, peracetic acid, sodium peroxide, potassium oxide, potassium peroxide, calcium peroxide, magnesium peroxide, urea peroxide, hydrogen peroxide ($H_2O_2$), hydroperoxides (ROOH), peroxides (ROOR), and superoxides, where R is an alkane, alkene or alkyne, branched or unbranched, and of between 1 and 12 carbons and Ar is an aromatic ring, usually of 6 carbons, or a combination of such rings. As used herein, the term "reactive oxygen species" excludes the gas ozone.

Humus is the major organic component of soil. "Humic acid" is a phenolic complex which is a component of humus. Commercially, humic acid is generally extracted from what is described as a salt-free deposit of highly oxidized carbon known as "Leonardite." Extraction of humic acid from Leonardite is described in detail in U.S. Pat. No. 5,607,856.

"Peracetic acid" is made by reacting glacial acetic acid with hydrogen peroxide. Since this reaction does not go to completion but instead results in a equilibrium being reached, at any point in time all three chemical species, peracetic acid, acetic acid, and hydrogen peroxide, will exist. A method for making peracetic acid suitable for use in connection with the compositions of the present invention can be found in Moon, U.S. Pat. No. 6,582,961, which is hereby incorporated by reference.

The phrase "field capacity" refers to the percent water remaining in the soil two to three days after having been saturated and after free drainage has practically ceased.

As used herein, "extracting" or "extraction" of a material means contacting the material, which if solid is preferably dried and crushed or ground, with an appropriate solvent to remove the substance or substances desired to be extracted from the material. Such an extraction may be carried out by conventional means; for example, by using an extraction apparatus which retains the solid material in a holder and allows the solvent to flow through the material, or by blending the solvent and material together and then separating the liquid and solid phases or two immiscible liquid phases, such as by filtration or by settling and decanting.

Unless otherwise specified, references herein to "parts per million" (or "ppm") used in reference to the compositions of the invention refers to the concentration of the solution containing the plant material extract, including any chelating agents, surfactants, or other chemicals which might also be present in the mixture as will be made clearer in the discussion below. Typically, the composition will be an aqueous solution comprising an alcohol.

As used herein, "an effective amount" of a composition of the invention is an amount that, when applied to soil infested with nematodes or to the roots of a plant infested with nematodes, results in a decrease of at least 10% in the number of nematodes infesting the plant, more preferably 20%, still more preferably 50% and most preferably 90% or more.

Compositions of the Invention

1. Plant Materials for Extraction

In general, the starting material for the compositions of the invention can be any juglone-producing member of the family Juglandaceae, and are preferably from trees of the genus *Juglans*. As noted above, juglone is not believed to be responsible for the dramatic effect seen with the compositions of the invention. It is believed, however, that the presence of juglone is a useful marker for members of the Juglandaceae that are useful for preparing the compositions of the invention. Accordingly, members of the family that produce juglone, including *Carya, Engelhardtia, Juglans, Platycarya* and *Pterocarya* can be used. Within the family, members of the genus *Juglans* are preferred. The species *J. nigra* (black or American walnut), *J. regia* (English walnut), and *J. cinerea* (butternut), are preferred, with the first two being more preferred and *J. nigra* being the most preferred. Testing of hulls and leaves of *J. nigra* and *J. regia* have indicated that they have approximately the same effectiveness in killing nematodes. Materials from one or more members of the Juglandaceae can be used together to form the compositions of the invention. For example, material from *J. nigra, J. cinerea*, and *J. regia*, or from any two of these, can be mixed together and used as the base for the alcohol extracts described below.

The studies underlying the present invention indicate that any part of the plants can be used. The highest amounts of activity have been noted using the nut hulls and the leaves, with the hulls producing the strongest nematicidal effect. Every other part of the tree tested thus far, however, has also had activity and can be used, including the wood, bark, shells. Walnuts will generally not be used for preparing the compositions of the invention simply because the nuts usually cost more per pound than wood chips, nut hulls, bark, and other by products of nut or wood production. But, walnuts can be used to make the compositions of the invention if desired. If nuts are used in making the compositions, it is desirable that other portions of the plants also be included in the materials to be extracted.

The invention provides an extra economic use for waste parts of the trees used to form the compositions of the invention. For example, hulls (also known as husks) are a waste product of walnut production, while sawdust and wood chips are waste products of producing walnut wood for furniture and other uses. These waste materials can be used in producing the compositions of the invention. Moreover, after being used to produce the compositions of the invention, the materials can be dried and then used, for example, as biomass in power generation or, in the case of wood chips and sawdust, as a base for forming manufactured wood products and the like. Since these waste materials are produced in the course of other uses, they are inexpensive and reduce the cost of preparing the compositions, while providing an extra benefit to the grower or processor, who can obtain value for materials that may otherwise need to be disposed of economically.

2. Use of Acids or Alcohol for Extraction

The compositions of the invention are extracts of the plant materials described above in an aqueous solution of an alcohol, in an acid, or in an aqueous solution of an acid (as noted in the Introduction, one of the alcohol extracts was made using glacial acetic acid, which is almost pure acetic acid. It is believed that a solution in which the acetic acid is diluted to between about 30-80% would result in even better extraction of nematode-killing substances from the plant material.).

As noted in the Introduction, alcohol extraction results in compositions with the highest nematode-killing activity. Methanol and isopropanol can be used. Preferably, however, the alcohol is ethanol. While juglone is known to be soluble in ethanol, a number of other napthoquinones are also present in the plant materials that can be used in making the compositions of the invention, and are also known to be soluble in ethanol. Walnut hulls, for example, comprise not only juglone (5-hydroxy-1,4-naphthoquinone), but also 1,4-naphthoquinone, 2-methyl-1,4-naphthoquinone, and plumbagin (5-hydroxy-2-methyl-1,4-naphthoquinone). The hulls also contain tannins and iodine. A number of compounds of other types may also be present in the compositions of the invention. For example, the leaves of *J. regia* (English walnut) are known to contain, in addition to juglone, ascorbic acid, carotene, quercetin, cyanadin, kaempferol, caffeic acid, and traces of p-coumaric acid, hyperin (0.2%), quercitrin, kaempferol-3-arabinoside, and quercetin-3-arabinoside. Without wishing to be bound by theory, it is believed that it is one or more of the other constituents present, or a synergism due to the combination of some or all of the constituents, that is responsible for the dramatic anti-nematode activity seen with the compositions of the invention compared to juglone alone.

It is also noted that ethanol extracted compositions are surprisingly more effective than water extractions, and that the naphthoquinones are soluble in alcohol. Thus, it is surmised that it is the combination of juglone and other naphthoquinones that are particularly responsible for the dramatic anti-nematode effects using the compositions of the invention in the methods of the invention, although other components may also be involved. It should be noted that, while juglone is not considered to be responsible by itself for the nematicidal effects of the compositions of the invention, it is considered to be a marker for the presence of other compounds, such as other napthoquinones, which by themselves or together are responsible for these effects.

The solutions used to extract active ingredients from the starting materials described below comprise a solution of an acid or alcohol in water. A combination of acid and alcohol can also be used if desired.

The acid or alcohol is preferably present at a concentration of between 10% and 90%, more preferably between about 20% and 80% and more preferably still between 40% and 75%. For alcohol extractions, particularly good results have been found using a concentration between about 50% and about 70% by weight of alcohol; accordingly, alcohol solutions in this range are the most preferred. While alcohols such as ethanol can be obtained in a pure form (e.g., "absolute"

ethanol), they are typically commercially available as a high percentage solution in water. Ethanol, for example, is typically available commercially as a 95% solution of alcohol in water. In the studies underlying the invention, a 70% solution of ethanol was used and is preferred for ease of handling. Absolute ethanol typically has a few parts per million of benzene left over from the purification process to remove water from the 95% solution obtained from fractional distillation and is less preferred. In the U.S., ethanol is often denatured to ensure that it is not used for drinking purposes without payment of the appropriate Federal taxes. If denatured ethanol is used, it should be denatured with a denaturant that is not toxic to plants at the concentration at which it would be present when the extract is applied to the soil.

Acid extraction of the plant materials discussed in the preceding section also results in compositions with nematode-killing activity surprisingly higher than extracts made from the same material using only water. Conveniently, the acid is one that is not toxic to plants, and that is environmentally friendly. Preferably, the acid is an organic acid. Preferred organic acids include acetic, citric, peracetic, and isocitric acids, with acetic acid being most preferred. Acetic acid and citric acid, in particular, are widely available, inexpensive, and not harmful to plants at the concentrations the compositions are applied in the field.

For convenience, the combination of the acid or alcohol solution and water solution to form the medium into which the plant material is placed for extraction will be referred to as the "extraction solution," and the solution formed by the dissolution of solutes from the plant material into the extraction solution will be called the "extract." The plant materials can soak in the extraction solution for as little as 10 minutes. On the other hand, the potency improves with longer extractions. Longer steeping is, therefore, desirable, with 1 hour, 2 hours, 3 hours, 4 hours, and 12 hours being progressively more preferred and 24 hours still more preferred. After about 48 hours, the potency does not appear to increase notably; if it is still increasing, the rate of increase of potency becomes very slow. On the other hand, longer soaking does not appear to be deleterious. It has not been noted that the extract can become too strong. Thus, the materials may be permitted to soak in the extraction solution for as long as desired; for example, the materials can be left to steep for as long as one or two months. Production of potent extracts can be maximized if the steeping time is not much greater than necessary to produce maximum potency.

Under some circumstances, however, it may be convenient to steep the materials for a longer period. For example, the producer may find it convenient to place the plant materials in the extraction solution on a Friday and to leave them in the solution over the weekend, or for a week or more over a vacation or the like. During periods of low demand (for example, over the winter), any plant materials already steeping in an extraction solution can simply be left in the solution until there is a need for the extract Periods of about 48 hours, however, give a reasonable balance of providing extracts of the maximum potency in the shortest period of time and are generally preferred.

The subject invention includes a process for preparing an extract of tissues of the plants of interest, such as hulls, leaves, bark, wood, shells and the like, by extracting the tissues using an acid solution or a solution of a water-miscible alcohol, such as methanol, ethanol, n-propanol or iso-propanol or mixtures of such alcohols. Ethanol is preferred.

At present, even though husks are a waste material, they are not particularly easy to obtain. Thus, while larger amounts can be used, for the studies underlying the invention, an attempt was made to see how small an amount of material could be used. Compositions were made with 5, 4, 3, 2, and 1% of hulls by weight in the starting materials, and all gave good nematicidal activity. Without wishing to be bound by theory, it is surmised that the substances extracted from the plant materials may reach a maximum. Thus, even ¼% by weight, or more preferably ½% by weight is likely to be sufficient in making the compositions of the invention. While these percentages are sufficient for leaves and hulls, which have the highest activities, wood, bark, and other portions of the plant are expected to have less activity, and should be used in larger quantity for extraction. The juglone content can be used as rough guide as to how much to be used. That is, if the wood of a particular plant is known to contain one-fifth the juglone content of the hulls, and a composition using X pounds of hulls is known to be sufficient for adequate nematicidal activity for a given use, it is expected that a composition with the same nematicidal strength can be made from the wood using five X pounds of the wood.

If the extract has been made using an alcohol-based extraction solution, it is preferable to add an organic acid to the resulting extract (it should be noted that in this case, the acid is not being added to extract substances from the plant material, but as an additive to the resulting solution. Thus, the acid can be added to the extract after the plant material has been removed. If desired, however, an acid can be added to an alcohol solution so that the plant material is subjected to extraction by both the alcohol and by the acid.) Preferably the organic acid is a carboxylic acid. Preferred organic acids include acetic, citric, and isocitric acids, with acetic acid being most preferred. Acid anhydrides hydrolyse in the presence of water to yield the acid, and therefore can be used in place of or with the acid in the compositions of the invention. For example, acetic anhydride can be used in place of acetic acid. Peracetic acid is in dynamic chemical equilibrium with acetic acid and can be used in place of or with acetic acid in the compositions and methods of the invention. If used, the peracetic acid is preferably made by the process described in Moon, U.S. Pat. No. 6,582,961. Acetic acid is commonly available and has the benefit of familiarity to farmers and other growers, and is preferred.

The studies underlying the present invention have shown that the presence of acetic acid in the solution reduces the period of time during which nematodes need to be exposed to the solution before they are killed. Therefore, the solutions of the invention preferably include acetic acid. Preferably, the acetic acid is added after the extraction of the plant material in the alcohol solution has occurred. If used, the acetic acid should be present in the range of from 1% to 50%, with about 2% to about 25% being more preferred, 5% to about 20% being even more preferred, 7.5 to about 15% still more preferred, and 10% being the most preferred. It is noted that acetic acid by itself will typically penetrate only into the top 2 inches of soil due to interactions with the soil. Acetic acid by itself can kill nematodes by lowering pH. It is not believed the activity of the compositions and methods of the invention can be explained by the acetic acid content, however, since the amount of acetic acid used would not be expected to alter the pH below the top 2 inches of soil. Additionally, the amount of acetic acid required to lower the pH of 4 million pounds of soil (the weight of an acre-foot of soil) would be enormous, while studies underlying the invention have provided a 90% reduction of nematodes over an acre-foot of soil using only 15 gallons of the compositions of the invention. Clearly, much larger quantities of acetic acid would be needed to lower the pH of that much soil by any significant amount. Thus, the effect seen in adding an organic acid to the plant material extracts does not be explained as a function of reducing the pH.

Optionally, small amounts (1-10%) of surfactants may also be added to help the solution filter through the soil and contact the plant roots. Surfactants are commonly used as wetting agents to improve the penetration of agricultural chemicals. A number of surfactants, such as Dow Corning® Q2-5211 Superwetting Agent (Dow Corning, Midland, Mich.), T-MULZ® phosphate esters (Harcros Organics, Inc., Kansas City, Kans.), and the DOWFAX™ series of nonionic surfactants (Dow Chemical Co., Midland, Mich.), are suitable for use in agricultural applications and are commercially available. Preferred surfactants for use in the compositions of the invention include Triton H-66™ and Tergitol™ 15 S. In a preferred embodiment, 2.5% of each of these two surfactants is added to the solution. Other surfactants that are compatible for use with plants can also be used. Compatibility can easily be tested by adding a solution of the surfactant at the contemplated concentration to a test plant or plot of plants and comparing the growth and health of the test plants against a control plant or plot of plants to which the surfactant is not administered. The surfactants should be also be compatible with acetic acid, peracetic acid, or such other acid as may be used in the solution. Compatibility can be tested in the same manner as that just described for determining the suitability of the surfactant.

Preferably, the composition contains an emulsifier. A number of emulsifiers and anti-foam agents suitable for agricultural use, such as T-MULZ® emulsifiers (Harcros Organics) and anionic and nonionic emulsifiers from Huntsman Surface Sciences (Houston, Tex.), are known in the art and are commercially available. In a preferred form, the emulsifier is a potassium phosphate, such as potassium phosphate monobasic, dibasic, or tribasic (tripotassium phosphate), which not only helps emulsify the solution and aid in its dispersal in the soil, but also acts as a chelating agent with metals in the soil. Tetrapotassium pyrophosphate is a preferred potassium phosphate for use in the compositions of the invention. The phosphate may be present in 1-20% by weight, more preferably 5-15%, and most preferably 10% of the overall solution. For example, if the composition is to weigh 100 pounds, 10 pounds may be of the potassium phosphate.

If an emulsifier that is not also a chelating agent is used, than it is preferable that a chelating or sequestering agent suitable for agricultural use, such as Agri-Sequest-All (Sper Chemical Co., Clearwater, Fla.) is also present. Citric acid is a preferred chelating agent and 1 to 5% of citric acid is preferably included in the compositions of the invention even if the emulsifier is also a chelating agent, and especially if no emulsifier is used.

The nematicidal substances may be extracted from the plant tissue using an extraction apparatus, where the alcohol solution is refluxed through the tissues, the plant material may be simply introduced into a solution in a container, or the plant material may be placed in a container and the solution poured over the material or otherwise introduced into the container so that it comes into contact with the plant material, which is preferably submerged. For example, hulls, leaves, branches and the like can simply be placed in the extraction solution and allowed to steep. Preferably, however, the surface area of the material is increased prior to or while in contact with the extraction solution. It will be appreciated the larger the surface area of the material in contact with the solution, the more opportunity there will be for components of the material to dissolve into the extraction solution, and the shorter the time that will be needed for that dissolution to occur. It will further be appreciated that the total surface area of a branch, hull, shell, piece of bark or other part of the plant will increase as it is crushed, ground, cut, sliced or shredded. Some materials will already be in a form that provides a suitably large surface area for contacting the solution without the need for further processing. For example, sawdust and wood chips from timber, sawmill, and manufacturing operations can simply be gathered up and placed in the alcohol solutions to form the compositions of the invention. The alcohol is preferably not evaporated from the resulting liquid extract, as it is believed to help move the extract through the soil to the roots when the extract is applied to plants.

Good results have been obtained preparing the compositions at room temperature. Room temperature preparation is generally preferable, since it avoids the cost of heating or cooling the materials. Higher temperatures may, however, permit extraction of even higher amounts of nematicidal substances from the plant material. If it is desired to prepare the compositions at a temperature well below or above room temperature (for example, at 40° F. or at 140° F.), a small batch can be made and tested for the composition 3. Combination with Systemic Inducers Moon, U.S. Pat. No. 6,582,961, discloses that the resistance of plants to a variety of pathogens can be increased by contacting the plants with a combination of reactive oxygen species and a plant systemic inducer. Surprisingly, studies undertaken in the course of the present invention indicate that adding a plant systemic inducer to the acid or alcohol extracts described above further suppresses nematode infestations. Without wishing to be bound by theory, it is surmised that the acid or alcohol extracts tend to kill nematodes present in the soil, thereby diminishing the number available to attack the plants, while the plant systemic inducer induces pathogen resistance in the plants which render them less susceptible to infestation. The effects of the two agents therefore appears to be synergistic in decreasing nematode infestation, thereby inhibiting nematode damage of plants.

Preferred systemic inducers include salicylic acid, jasmonic acid, isonicotinic acid, dichloroisonicotinic acid, phosphorous acid, and cinnamic acid, chitosan, humic acid, and beta-1,3 glucans and other mixed glucans. Salicylic acid is particularly preferred.

Methods of the Invention

Typically, the life cycle for nematodes starts with an egg, followed by four larval or juvenile stages (usually referred to as the L1, L2, L3 and L4 stages), and an adult stage, with a molt between each stage. The life cycle for many nematodes is 28-30 days. Thus, the compositions of the invention are typically applied twice, once to kill the adult nematodes and once approximately 30 days later to kill any nematodes that have hatched in the intervening time. If infestation recurs, third or even fourth applications can be made, but are usually not necessary. It is noted that some plant parasitic nematodes have life cycles as short as two weeks, while some dagger nematodes may require a full year, and that the duration of the life cycle can vary depending on soil and the prevailing temperature. For example, the northern root-knot nematode (*Meloidogyne hapla*) can vary from 17 to 57 days. Commercial growers are typically aware of the particular nematode species that are the most numerous in their fields, area, or state; the length of time between applications can be shortened (for species that reproduce more quickly) or increased (for species with longer reproductive cycles) as appropriate to control the nematode populations. Needless to say, growers facing a mixed population of nematodes with short and long life cycles will tend to apply the compositions on a schedule designed to reduce the damage from the nematodes with the shortest life cycle of the population.

It will be appreciated that some crops are only vulnerable to nematode damage during an early part of their growth, and thus will not need a further application if they are protected during the vulnerable period. For example, carrots are very vulnerable to nematode damage during their first two weeks of growth, and thereafter are not strongly affected by nematode infestation. Thus, an application of the compositions of the invention to the field prior to planting or immediately post-planting of the carrots will eliminate most or all of nematode damage to the crop. Typically, the compositions are applied at about 5000 ppm with the "germ water" and again 10 days later. By the time nematodes from surrounding areas can infiltrate the soil or a substantial number of eggs in the soil hatch to provide a new infestation of nematodes, the carrot roots are beyond the point at which the nematodes can affect the crop. For other crops, the compositions are typically applied when there is a root flush, that is, that the roots are first fleshing out from the seedling.

The compositions of the invention are applied at a rate of 1000 to about 30,000 ppm, and more preferably about 1500 to about 20,000 ppm. In some embodiments, the compositions are applied at about 2000 ppm to about 15,000 ppm, and more preferably about 3000 to about 10,000 ppm. In other embodiments, the compositions are applied at about 3,500 ppm to about 8,000 ppm, and more preferably about 4,000 to about 7,000 ppm. In yet other embodiments, the compositions are applied at about 4500 ppm to about 6,000 ppm, and more preferably about 3000 to about 10,000 ppm. Most preferably, the compositions are applied at about 5,000 ppm. As used herein, the term "about" recognizes that it is difficult to obtain a precise application and that the concentration of the composition will likely vary within about 200 ppm in any given application. It is also understood that such small variations will not have any measurable effect on the nematicidal efficacy of the application.

The studies underlying the invention indicate that a concentration of about 5000 ppm kills 90% of nematodes. Since farmers have been accustomed for years to mixing pesticides, fertilizers, and other agricultural chemicals for use in their fields, the application of the compositions of the invention are well within a farmer's skill. Nonetheless, errors do happen. The preferred concentration of 5000 ppm is such that if the farmer accidentally halves the concentration, it will still be high enough to provide significant effect, while if it is accidentally doubled, it will not be toxic to the plants. Lower or higher concentrations can, of course, be employed, at the user's option, but are preferably within the limits noted above. Phytotoxicity has not been noted at concentrations as high as 20,000 ppm.

Application of the Compositions of the Invention

The compositions of the invention are typically applied to the soil so that they can kill nematodes in and around plant roots. The soil is preferably first saturated to wet the particles of the soil so that the compositions can move freely in the soil and reach the roots of the plants. Therefore, preferably the soil is saturated to field capacity with ordinary water prior to application of the compositions. The compositions are then applied at a concentration of between 1000 and about 30,000 ppm, as noted above.

It will be recognized that the intention is to have an effective concentration of the compositions at the depth in the soil the roots of the plant are to be found. Desirably, the compositions are applied to provide a concentration of about 5000 ppm at and around the roots. For most plants, early in their life, the roots will be close to the surface and the concentration at the roots will be close to that applied to the surface. Young plants and plants of some species, such as the grasses used on golf courses, lawns and parks, tend to have short, fibrous roots. For these plants, applications of 5000 ppm to the soil surface will provide approximately that concentration to the roots and to the soil around the roots, to kill root lesion and root knot nematodes, among others.

While some grasses and younger plants have shallow root structures, many plants and many more mature plants have deeper root structures, often 4 to 12 inches into the soil. The rule of thumb in the art for preventing nematode damage is that the majority of roots involved in nutrient and water uptake occur in the top 12 inches of soil, while deeper roots tend to be involved in anchoring the plants. In sandy, aerated soils, the roots involved in nutrient transport can extend down to 18 inches. Penetration of the compositions of the invention into the first foot of the soil, however, will provide protection to the feeder roots, which do not develop protective coverings, and is anticipated to be beneficial in enhancing the survival and health of the plants.

The compositions of the invention can be applied in several ways. As farmers and other practitioners will be aware, 3000 gallons of water will typically soak 1 acre to a depth of 12 inches (an "acre-foot"). To provide 5000 ppm of the compositions of the invention, 15 gallons of the compositions is added to the water supply and applied to the field. At 9 pounds per gallon, this amounts to 135 pounds of the composition. Alternatively, 30,000 ppm of the composition can be applied to the surface of the soil, with a water "push" of applying water to the soil to move the composition into the acre-foot of soil to provide a concentration of 5000 ppm down to 12 inches. Such "water pushes" to create concentration gradients are commonly used by farmers in applying agricultural chemicals and are well known in the art.

It will be appreciated that for a golf course, which has grasses with roots penetrating only to perhaps the first 5-6 inches of soil, only 1000 to 1500 gallons of water will be needed, and only 6-7½ gallons of the compositions are needed to provide 5000 ppm of the composition in the water.

It should be noted that the farmer is usually well aware of the flow rate per acre of the irrigation or other soil application system in place on his or her property, as well as the acreage to be covered. The farmer can calculate the amount of water which will be used in watering the land for any particular amount of time (for example, 300 gallons per minute times 50 acres times 30 minutes is 450,000 gallons of water). The farmer can then calculate how much is needed to result in an application of the desired concentration of the solution.

What is desired is that the solutions result in the presence of the preferred concentration of the plant extract for between 10 and 100 hours, more preferably for between 12 and 72 hours, and more preferably still for between 20 to 50 hours. If the composition is of an alcohol extract that includes an organic acid, such as acetic acid, peracetic acid, or citric acid, the time for the presence of the plant extract can be at the shorter end of the time range, while compositions without an organic acid should be applied for the longer end of the range. Thus, if acetic acid is used in the solution, the plants should be in contact with the recommended concentration of the plant extract for 20-28 hours, with 24 hours being preferred for convenience, whereas if acetic acid or another acid is not present, the plants should be in contact with the recommended concentration of the plant extract for 40-50 hours, with 48 hours being preferred for convenience.

The periods mentioned above for contacting plant roots with the compositions of the invention are intended to describe periods effective to cause a reduction in nematode number sufficient to cause a noticeable difference in the health of the plant. The soil around the plants should not be treated in a manner that would reduce the concentration of the compositions during the periods stated. For example, once the desired concentration is achieved, it is desirable that the soil not be watered again for the period in question so that the effective concentration is not reduced. Similarly, it is undesirable to apply the compositions of the invention when a substantial rain is expected within the period in which it is desired that the compositions be present. On the other hand, the compositions of the invention are not deleterious to the plants and can be left in place after the desired period has elapsed.

The compositions are typically applied to the soil by being run through a hose, pipe, drip, sprinkler, irrigation channel, or other mechanism. In practice, agriculture is not a science and the devices used are typically not precision equipment. Accordingly, when the water flow is turned off, water will typically continue to drip or run from the hose or through the irrigation channel or other applicator for some time. It is therefore understood that the times of application will generally be an approximation and will be measured from the start of the flow of the mixture to when the flow of the mixture is turned off, whether or not some of the mixture continues to drip or run from the applicator.

Persons of skill are aware that non-chemical methods, such as crop rotation and cover crops, are used instead of or in conjunction with chemical methods to control nematodes. The compositions of the invention can be used in conjunction or in place of with these methods.

Uses of the Invention

The invention can be used to protect almost any plant susceptible to nematode damage. Although some plants are considered to be susceptible to juglone, the concentration of juglone when the compositions of the invention are applied at the concentration contemplated herein that even susceptible plants will not be damaged. The plants to be protected by means of the invention can be dicots, such as carrots, lettuce, tomatoes, grapes, citrus fruits, and beans, or monocots, such as corn. The plants can be grown for human or animal consumption, such as grains, vegetables, and fruits, can be intended for decorative use, such as flowers, or can be intended for ornamental use, such as trees grown for use as Christmas trees or plants intended for use as house plants. Further, they can be plants grown for fiber, such as cotton plants, or for use as turf. The compositions are especially useful, for example, on golf courses, lawns and ballfields. Most commonly, the invention will be used to protect plants grown in fields as crops or in other open conditions, such as tree farms or turf; the invention can, however, also be used to protect plants grown in settings such as greenhouses and hothouses should nematode infestations be found in the soil in such environments. The compositions can also be used in hydroponic applications; this use is, however, less preferred.

It is anticipated that the compositions of the invention will be useful, for example, in preventing or reducing infestation of young citrus trees from the burrowing nematode, *Radopholus citrophilus*, causal agent of 'spreading decline of citrus'; the citrus nematode, *Tylenchulus semipenetrans*, causal agent of 'slow decline of citrus'; two species of lesion nematode, *Pratylenchus coffeae* and *P. brachyurus*, causal agents of 'citrus slump'; and the sting nematode, *Belonolaimus longicaudatus*, and will reduce the infestation of mature trees by these nematodes.

Because the invention protects crops against at least a portion of the damage which would otherwise be caused by nematodes, a higher percentage of the crops grown for human consumption can be sold as first quality crops. Moreover, since less of the crop is unmarketable, the invention results in a higher yield per acre. These factors combine to result in higher revenues per acre for the farmer, and also reduce the level of infestation necessary before it is economically advantageous to use the inventive compositions and methods.

EXAMPLES

Example 1

This Example describes an exemplar composition of the invention.

To make an exemplar 100 pounds of a 1% solution of a juglone-producing plant of the family Juglandaceae, the following is mixed:

Mix 1:
41 pounds deionized water, and
10 pounds tetrapotassium pyrophosphate,
for a total of 51 pounds of Mix 1.

Mix 2:
14 pounds of 70% ethanol,
10 pounds of 99% acetic acid, and
1 pound of walnut hulls,
for a total of 25 pounds.

Mix 3:
22 pounds of deionized water, and
2 pounds of citric acid,
for a total of 24 pounds.

The three mixes were mixed together, for a total of 100 pounds of product.

The walnut hulls can be left in the solution or, preferably, filtered or strained out of the liquid before application to plants or the field.

In the Example above, the three mixes were prepared separately for convenience of dissolving the different solutes. Since Mix 2 should steep for 24-48 hours, it can be made before the other two. For convenience, however, all three mixes are made at the same time. Once mix 2 has steeped for the desired period of time, it can be mixed into the other two, or the three mixes can be transported to the site of use, mixed and applied. Deionized water was used in some of the studies underlying the invention to reduce artifacts that might be introduced from minerals in the water; in field use, however, regular irrigation or pond water or the like would be used to reduce cost and complexity.

The amounts set forth above can be scaled up to provide larger quantities or down to provide smaller quantities. Quantities as small as 100 grams and as large as 2000 pounds have been made by simply scaling up or down, as appropriate, the amounts set forth above.

Example 2

A field trial was conducted on an orange grove, comparing the effect of the composition described in Example 1 (under its trade name, NatureCur™) against two widely used, commercially available nematicides, an emusifiable concentrate of 1,3 dichloropropene which can be applied to the soil after plants are planted (called a "post-plant" application) (Dow AgroSciences LLC, Indianapolis, Ind.), shown on the accompanying charts as "Cordon," and imidacloprid, an insecticide marketed under the name Admire® (Bayer CropScience LP, Research Triangle Park, N.C.). For the soil treated with Cordon and the soil treated with Admire®, single applications of the agents were made in mid-May. The product NatureCur™ was applied in once in mid-May, once 30 days later in mid- June, and once again 30 days later in mid July, each time at a concentration of 5000 ppm. The soil in the grove was a clay loam, a very dense, heavy soil in which it is difficult to get agents to travel. Thus, the soil in this grove provided a particularly difficult test condition for NatureCur™, which has to infiltrate through the soil in water.

Samples were taken of the soil around the plants and of the roots. The percentage of reduction in number of nematodes in soil treated with the three agents compared to untreated soil is shown in Table 1 and FIG. 1.

TABLE 1

| Agent: | Percent reduction in nematodes in soil: |
|---|---|
| 1,3 dichloropropene | 58% |
| Imidacloprid | 32% |
| NatureCur ™ (Walnut Extract) | 55% |

Figure 2:
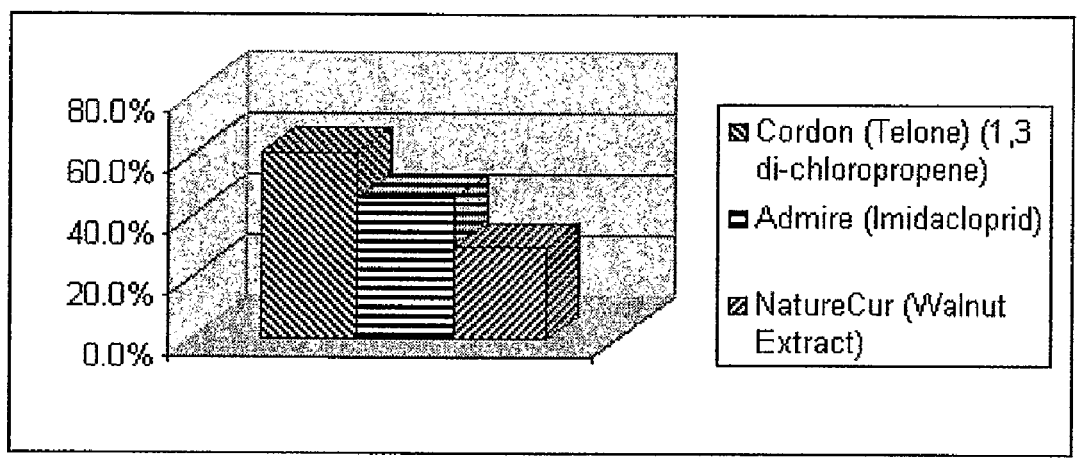
FIG. 2 is a graph of the percent reduction in nematode infestation of plant roots after the soil in which the plants were being grown was treated with the agent indicated, compared to plants grown in untreated soil. Vertical axis: percent reduction of nematodes. Legend: bar with lines sloping downward from left to right: 1,3 dichloropropene; bar with horizontal lines, imidacloprid; bar with lines sloping upward from left to right, an alcohol extract of the invention.

The percentage of reduction in number of nematodes in roots of plants whose soil was treated with the three agents compared to roots of plants in untreated soil is shown in Table 2 and FIG. 2.

TABLE 2

| Agent: | Percent reduction in nematodes in roots: |
|---|---|
| 1,3 dichloropropene | 61% |
| Imidacloprid | 46% |
| NatureCur ™ (Walnut Extract) | 30% |

A comparison of the two Tables shows that the walnut extract significantly reduced nematode populations in both the soil and in plant roots. The fact that the walnut hull extract showed a greater percentage of reduction of nematodes in the soil than in the roots indicated that the nematodes had successfully infested the plant roots prior to the application of the product in mid-May, indicating that application of the product earlier in the growing season would result in even greater reductions in nematode infestation of the plants. It was also noted that Admire® is a systemic agent which is taken into the plant, and that the higher kill numbers in the roots reflect the fact that the agent can enter the plant to kill nematodes already in the roots. It is expected that application of the walnut extract at the beginning of the growing season, before the nematodes have had a chance to reach the roots, would reduce the nematode infestation by percentages closer to that observed in the soil.

Example 3

A field trial was conducted on a carrot farm to compare the effect on nematode levels of the composition described in Example 1 (under its trade name, NatureCur™) against two widely used, commercially available nematicides, Telone® II, a soil fumigant form of 1,3 dichloropropene (Dow AgroSciences LLC, Indianapolis, Ind.), and Vapam® (anhydrous sodium N-methyldithiocarbamate, Amvac Chemical Corp., Los Angeles Calif.). According to the manufacturer, when Vapam® contacts soil, it converts into methyl isothiocyanate, a volatile, highly toxic fumigant.

In carrots, nematodes which attack the tip of the plant during the first 20 days post emergence cause the carrot to "fork". Forked carrots are unmarketable, and nematodes are the primary cause of forking. Thus, determining the percentage of carrots that are forked serves as a measure of how much the compositions tested can reduce the economic loss or damage caused by nematodes to a carrot population.

The test area was divided into plots, each of which was a little less than an acre in size. Each agent was tested on ten replicate plots. Following application of the agent, a like-size strip of carrots was harvested from each plot and examined for forking.

| Agent | Plot | Forking/No. of Carrots |
|---|---|---|
| NatureCur ™ | West 1 | 2 of 19 |
| NatureCur ™ | West 2 | 1 of 19 |
| NatureCur ™ | West 3 | 3 of 19 |
| NatureCur ™ | West 4 | 2 of 14 |
| NatureCur ™ | West 5 | 1 of 19 |
| NatureCur ™ | East 1 | 0 of 8 |
| NatureCur ™ | East 2 | 0 of 10 |
| NatureCur ™ | East 3 | 0 of 11 |
| NatureCur ™ | East 4 | 0 of 10 |
| NatureCur ™ | East 5 | 0 of 6 |

Total: 9 of 135, or 6.67%

| Vapam ® | West 1 | 1 of 12 |
|---|---|---|
| Vapam ® | West 2 | [Not used] |
| Vapam ® | West 3 | 3 of 12 |
| Vapam ® | West 4 | 1 of 10 |
| Vapam ® | West 5 | 2 of 13 |
| Vapam ® | West 6 | 0 of 6 |
| Vapam ® | East 1 | 0 of 7 |
| Vapam ® | East 2 | 1 of 12 |
| Vapam ® | East 3 | 1 of 17 |
| Vapam ® | East 4 | 3 of 10 |
| Vapam ® | East 1 | 0 of 8 |

Total: 12 of 107, or 11.21% *

| Telone ® II | West 1 | 1 of 11 |
|---|---|---|
| Telone ® II | West 2 | 1 of 10 |
| Telone ® II | West 3 | 0 of 10 |
| Telone ® II | West 4 | 2 of 12 |
| Telone ® II | West 5 | 0 of 18 |
| Telone ® II | East 1 | 2 of 20 |
| Telone ® II | East 2 | 1 of 8 |
| Telone ® II | East 3 | 1 of 10 |
| Telone ® II | East 4 | 0 of 6 |
| Telone ® II | East 5 | 2 of 11 |

Total: 10 of 116, or 8.62%

*/ The carrots exposed to Telone ® II were older than the carrots exposed to the other two agents when they were reviewed for forking. Since forking is considered due to nematode attack of the carrot tip during the first 20 days of growth, however, examination of the forking in older carrots still permits comparison of nematode infestation levels of the carrots during the first 20 days in soils contacted with the different agents.

The results of the study indicate that use of the walnut extract was able to reduce forking by as much as half compared to carrots exposed to current, widely used nematicides.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising an extract of a first juglone-producing plant of the family Juglandaceae and a plant systemic inducer wherein the extract is produced by placing the plant into an extraction solution where the extraction solution is an aqueous acid-alcohol solution having 40% to 75% alcohol and the extract comprises the extract solution into which the plant is placed.

2. A composition of claim 1 wherein said first juglone-producing plant is a member of a genus selected from the group consisting of *Carya, Engelhardtia, Juglans, Platycarya* and *Pterocarya*.

3. A composition of claim 2, wherein said first juglone-producing plant is a member of the genus *Juglans*.

4. A composition of claim 3, wherein said first juglone-producing plant is of a species selected from the group consisting of *J. nigra, J. cinerea*, and *J. regia*.

5. A composition of claim 4, wherein said first juglone-producing plant is *J. nigra*.

6. A composition of claim 1, wherein the material from which the extract is made is selected from the group consisting of nut hull, leaf, nut shell, root, bark, and wood.

7. A composition of claim 1, wherein said extract is made from nut hull.

8. A composition of claim 1, wherein said acid is an organic acid.

9. A composition of claim 8, wherein said acid is selected from a group consisting of acetic acid and citric acid.

10. A composition of claim 1, wherein the alcohol is ethanol.

11. A composition of claim 8, wherein the organic acid is a carboxylic acid.

12. A composition of claim 1, further comprising a surfactant.

13. A composition of claim 1, further comprising an emulsifier.

14. A composition of claim 13, wherein the emulsifier is a potassium phosphate.

15. A composition of claim 14, wherein the potassium phosphate is tetrapotassium pyrophosphate.

16. A composition of claim 1, wherein the plant systemic inducer is selected from the group consisting of salicylic acid, jasmonic acid, isonicotinic acid, dichloroisonicotinic acid, phosphorous acid, cinnamic acid, chitosan, humic acid, and a beta-1,3glucan.

17. A composition of claim 16, wherein said plant systemic inducer is salicylic acid.

18. A composition of claim 16, further comprising an aqueous acid-alcohol extract of a second juglone-producing plant of the family Juglandaceae.

19. A composition of claim 18, wherein said first and said second juglone-producing plants are of the genus *Juglans*.

20. A composition of claim 18, wherein said first and said second juglone-producing plants are selected from the group consisting of *J. nigra, J. cinerea*, and *J. regia*.

21. A composition of claim 18, wherein the material from which the extract from said second juglone-producing plant is made is selected from the group consisting of nut hull, leaf, nut shell, root, bark, and wood.

22. A nematicidal composition comprising an extract of a first juglone-producing plant of the family Juglandaceae and a plant systemic inducer wherein the extract is produced by placing the plant into an extraction solution where the extraction solution is an aqueous acid-alcohol solution having 40% to 75% alcohol and the extract comprises the extract solution into which the plant is placed.

* * * * *